(12) United States Patent
Van Der Waal et al.

(10) Patent No.: US 10,550,128 B2
(45) Date of Patent: Feb. 4, 2020

(54) HYDROGENATED DIELS-ALDER ADDUCTS AND LACTONE COMPOUNDS

(71) Applicants: Avantium Knowledge Centre B.V., Amsterdam (NL); Stichting Wageningen Research, Wageningen (NL)

(72) Inventors: Jan Cornelis Van Der Waal, Amsterdam (NL); Edserd De Jong, Amsterdam (NL); Jacco Van Haveren, Ede (NL); Shanmugam Thiyagarajan, Wageningen (NL)

(73) Assignees: Avantium Knowledge Centre B.V., Amsterdam (NL); Stichting Wageningen Research, Wageningen (NL)

( * ) Notice: Subject to any disclaimer, the term of this patent is extended or adjusted under 35 U.S.C. 154(b) by 0 days.

(21) Appl. No.: 16/291,332

(22) Filed: Mar. 4, 2019

(65) Prior Publication Data

US 2019/0194221 A1  Jun. 27, 2019

Related U.S. Application Data

(62) Division of application No. 15/536,708, filed as application No. PCT/NL2015/050882 on Dec. 18, 2015, now Pat. No. 10,266,546.

(30) Foreign Application Priority Data

Dec. 19, 2014 (NL) .................................... 2014023

(51) Int. Cl.
| C07D 493/18 | (2006.01) |
| C07D 307/88 | (2006.01) |
| C07D 307/89 | (2006.01) |
| C07D 493/04 | (2006.01) |
| C07C 51/31 | (2006.01) |

(52) U.S. Cl.
CPC ............ C07D 493/18 (2013.01); C07C 51/31 (2013.01); C07D 307/88 (2013.01); C07D 307/89 (2013.01); C07D 493/04 (2013.01)

(58) Field of Classification Search
CPC .. C07D 493/18; C07D 493/04; C07D 307/88; C07D 307/89; C07C 51/31
See application file for complete search history.

(56) References Cited

U.S. PATENT DOCUMENTS

| 2,729,674 A | 1/1956 | McKinnis |
| 4,138,354 A | 2/1979 | Sochol et al. |
| 4,262,157 A | 4/1981 | Hori et al. |
| 2005/0119228 A1* | 6/2005 | Salvati ................. C07D 487/18 514/80 |
| 2010/0127220 A1 | 5/2010 | Tierney et al. |
| 2010/0178331 A1 | 7/2010 | Nagata et al. |

FOREIGN PATENT DOCUMENTS

| DE | 4326273 A1 * | 2/1995 | ........... C07C 227/44 |
| WO | 2007/104514 A2 | 9/2007 | |
| WO | 2008/097561 A1 | 8/2008 | |
| WO | 2008/128618 A1 | 10/2008 | |
| WO | 2013/048248 A1 | 4/2013 | |

OTHER PUBLICATIONS

Takano, S., "Diels-Alder Reaction of Furfural Derivatives and Its Application" 1982 Yakugaku Zasshi 102(2):153-161.*
Kitahara, Y., "Ether cleavage of 7-oxabicyclo [2, 2, 1] heptane derivatives." Journal of the Chemical Society C: Organic (1968): 2508-2510.*
Kraus, G. A., "Synthetic approaches to rhodomycinone and olivin." The Journal of Organic Chemistry 48.19 (1983): 3265-3268.*
Rice, L.M., "Hypotensive Agents. V. 1 Hydrogenated Bis-isoindole Quaternary Salts2." Journal of the American Chemical Society 77.3 (1955): 616-621.*

(Continued)

Primary Examiner — John M Mauro
(74) Attorney, Agent, or Firm — Hoffmann & Baron, LLP

(57) ABSTRACT

A hydrogenated Diels-Alder adduct of the formula (III)

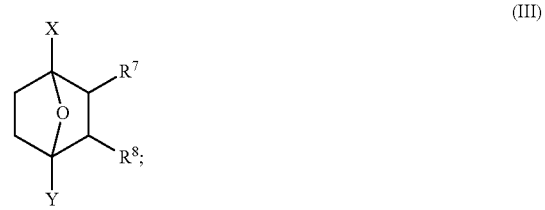

a hydrogenated Diels-Alder adduct of the formula (IV)

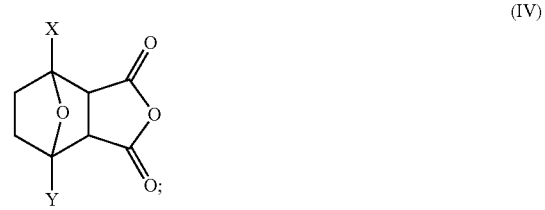

and
a lactone compound of formula (V)

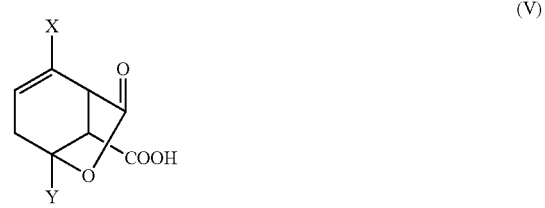

are disclosed and described.

3 Claims, No Drawings

(56) References Cited

OTHER PUBLICATIONS

Chen, Y.-C. "Norcantharidin reduced cyclins and cytokines production in human peripheral blood mononuclear cells." Life sciences 84.7-8 (2009): 218-226.*
Kato, T., "An approach to the synthesis of fujenoic acid." Journal of the Chemical Society, Perkin Transactions 1 2 (1977): 206-210.*
DE4326273, 1995, WIPO English Machine Translation accessed online Jun. 12, 2019 p. 1-33.*
Baba, Yoshiyasu et al., "Structure-Based Design of a Highly Selective-Catalytic Site-Directed Inhibitor of Ser/Thr Protein Phosphatase 2B (Calcineurin)", Journal of the American Chemical Society, vol. 125, No. 32, Aug. 1, 2003, pp. 9740-9749.
Database CA [Online] Chemical Abstracts Service, Columbus, Ohio 1991 (XP-002742959).
Diels, Otto and Olsen, Sigurd, "Uber synthetische Versuche in der Reihe des Cantharidins, Nor-und Isocantharidins", J. Prakt. Chem, 1940, 156, pp. 285-314 (XP-002742960)
Ghosh, Ketaki et al., "Total Synthesis of Neo-Tanshinlactones through a Cascade Benzannulatin-Lactonization as the Key Step", European Journal of Organic Chemistry, May 8, 2013, No. 19, pp. 4037-4046.
Jung, Michael E. et al., "Total Synthesis of Racemic Laurenditerpenol, an HIF-1 Inhibitor", The Journal of Organic Chemistry, 2009, Nov. 20, 74, No. 22, pp. 8739-8753.
Kapp, Jorg et al., "Calcium-independent activation of the contractile apparatus in smooth muscle of mouse aorta by protein phosphatase inhibition", Naunyn-Schmiedeberg's Archives of Pharmacology, Dec. 1, 2002 366(6):562-569.
Zhang, Jie et al., "From Spanish fly to room-temperature ionic liquids (RTILs): synthesis, thermal stability and inhibition of dynamin 1 GTPase by a novel class of RTILs", New Journal of Chemistry, vol. 32, No. 1, Jan. 2008 pp. 28-36.
Bajsa, Joanna et al., "The antiplasmodial activity of norcantharidin analogs", Bioorganic & Medicinal Chemistry Letters, 20:6688-6695 (2010).
Matsuzawa, M., "Endothal and cantharidin analogs: relation of structure to herbicide activity and mammalian toxicity." Journal of agricultural and food chemistry 35.5 (1987): 823-829.
PCT Search Report and PCT Written Opinion for corresponding International Application No. PCT/NL2015/050882, dated Apr. 19, 2016 (13 pages).
PCT International Preliminary Report on Patentability for corresponding International Application No. PCT/NL2015/050882, dated Apr. 19, 2016 (7 pages).
NL Search Report and Written Opinion for corresponding Dutch Application No. NL 2014023, dated Aug. 6, 2015 (10 pages).

* cited by examiner

HYDROGENATED DIELS-ALDER ADDUCTS AND LACTONE COMPOUNDS

CROSS-REFERENCE TO RELATED APPLICATIONS

This application is a Divisional of U.S. application Ser. No. 15/536,708, filed Jun. 16, 2017, which is the U.S. National Stage of International Application No. PCT/NL2015/050882 filed Dec. 18, 2015, which claims the benefit of Netherlands Application No. NL 2014023, filed Dec. 19, 2014, the contents of which is incorporated by reference herein.

FIELD OF THE INVENTION

The present invention relates to an improved process for the preparation of a benzene compound, more in particular to a process for the preparation of a benzene compound which comprises a process step wherein a furan compound is reacted with an olefin. The reaction of the furan compound with the olefin may be a Diels-Alder reaction.

BACKGROUND OF THE INVENTION

Such a process is known from e.g. WO 2013/048248. In this application it is described that there is an increasing tendency to create chemicals from renewable sources. Research has been undertaken to prepare chemicals from biomass materials, such as carbohydrates, e.g. cellulose, starch, hemicelluloses, sugars, glucose and fructose. Dehydration of such carbohydrates may yield valuable chemicals, including levulinic acid, furfural, hydroxymethyl furfural and derivatives thereof. In WO 2013/048248 the reaction is disclosed wherein a 2-alkoxymethyl furan is reacted with a substituted olefin to yield an unsaturated bicyclic ether. The bicyclic ether is subsequently dehydrated and aromatized to yield a substituted benzene compound. Via this process substituents on the 1,2-, 1,3- or 1,2,3-positions of the benzene ring are obtained. The thus obtained products may elegantly be converted by oxidation into phthalic acid, isophthalic acid and hemimellitic acid.

In US 2010/0127220 a process for the manufacture of substituted pentacenes is described. The process includes a step wherein dimethylfuran is reacted with maleic anhydride via a Diels Alder reaction to yield a bicyclic unsaturated ether. The bicyclic unsaturated ether is then dehydrated and aromatized under aromatization conditions to yield 4,7-dimethyl-isobenzofuran-1,3-dione (see reaction scheme A, wherein step (i) is a Diels-Alder reaction and step (ii) is the aromatization).

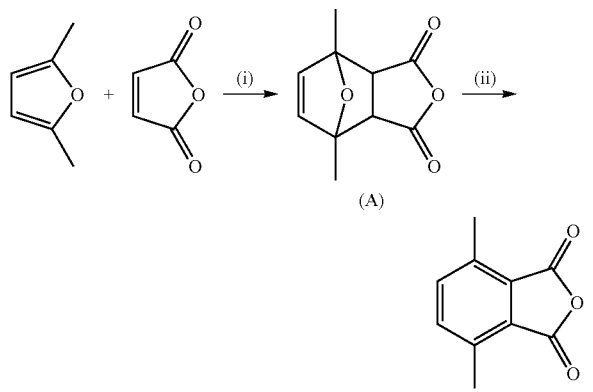

(A)

It appears that the yield of the bicyclic unsaturated ether can be relatively high. An example in WO 2013/048248 shows that the yield of the bicyclic unsaturated ether can be about 96%. According to an example in US 2010/0127220 a yield of about 72% could be obtained in the preparation of the bicyclic unsaturated ether (cf. US 2010/0127220, Example 1). However, both documents also show that the yield of the subsequent dehydration is significantly lower. According to Example 2 in WO 2013/048248 the desired benzene compound could be obtained in a yield of 37%, whereas the yield on the desired benzene compound in US 2010/0127220 amounted to about 41%. When the yields are calculated on the basis of the starting furan compound the overall yield is about 30 to 35% according to the examples in these documents.

It has now been found that the overall yield of the preparation process can be increased when the dehydration step of the bicyclic unsaturated ether is preceded by a hydrogenation step, wherein the unsaturated bond of the bicyclic unsaturated ether that is obtained in the reaction of the furan compound with the olefin is hydrogenated. Surprisingly, the saturated bicyclic ether thus obtained can still be dehydrated and aromatized, yielding the desired benzene compound.

SUMMARY OF THE INVENTION

Accordingly, the present invention provides a process for the preparation of a benzene compound which comprises
(i) reacting a furan compound of formula (I):

wherein $R^1$ and $R^2$ are the same or different and independently selected from the group consisting of hydrogen, alkyl, aralkyl, —CHO, —CH$_2$OR$^3$, —CH(OR$^4$)(OR$^5$), —COOR$^6$, wherein $R^3$, $R^4$ and $R^5$ are the same or different and are independently selected from the group consisting of hydrogen, alkyl, aryl, alkaryl, aralkyl, alkylcarbonyl and arylcarbonyl, or wherein $R^4$ and $R^5$ together form an alkylene group, and wherein $R^6$ is selected from the group consisting of hydrogen, alkyl and aryl,
with an olefin of the formula (II)

$$R^7—CH=CH—R^8 \qquad (II),$$

wherein $R^7$ and $R^8$ are the same or different and are independently selected from the group consisting of hydrogen, sulfonate, —CN, —CHO, and —COOR$^9$, wherein $R^9$ is selected from the group consisting of hydrogen, and an alkyl group, or $R^7$ and $R^8$ together form a —C(O)—O—(O)C— group or a —C(O)—NR$^{10}$—C(O)— group, wherein $R^{10}$ represents hydrogen, an aliphatic or an aromatic group, to produce an unsaturated bicyclic ether having an unsaturated carbon-carbon bond;
(ii) hydrogenating the unsaturated carbon-carbon bond in the unsaturated bicyclic ether to produce a saturated bicyclic ether; and
(iii) dehydrating and aromatizing the saturated bicyclic ether to produce the benzene compound.

DETAILED DESCRIPTION OF THE INVENTION

The first step of forming the unsaturated bicyclic ether from the furan compound of formula (I) and the olefin of formula (II) seems to occur via a Diels-Alder-type reaction. It is known that Diels-Alder reactions may be reversible. Then the so-called retro-Diels-Alder reaction takes place. Without wishing to be bound by any theory, it is believed that by the hydrogenation of the double bond in the Diels-Alder adduct, i.e. the unsaturated bicyclic ether, the occurrence of the retro-Diels-Alder reaction is prevented. It is further surprising that in spite of the saturation that is introduced into the bicyclic ether, the dehydration and aromatization of the saturated ether does occur in satisfactory yields.

It is known that in Diels-Alder reactions the reaction rate is expedited by providing electron withdrawing groups on the olefin, i.e. the dienophile, and electron donating groups on the furan compound, i.e. the diene. Electron withdrawing groups include cyano, sulfonate, carboxylic acid, carboxylic anhydride, carboxylic ester, ketone and aldehyde groups. Electron donating groups include hydroxy, ether, aliphatic and aromatic hydrocarbon groups. Accordingly, the present invention preferably employs a furan compound of formula (I), wherein $R^1$ and $R^2$ are the same or different and independently selected from the group consisting of hydrogen, alkyl, aralkyl, —CHO, —$CH_2OR^3$, wherein $R^3$ is selected from the group consisting of hydrogen and alkyl. More preferably, $R^1$, $R^2$ and $R^3$ are independently selected from the group consisting of hydrogen and an alkyl group having 1 to 4 carbon atoms.

The olefin of formula (II) suitably comprises compounds, wherein $R^7$ and $R^8$ are the same or different and are independently selected from the group consisting of hydrogen, —CHO and —$COOR^9$, wherein $R^9$ is selected from the group consisting of hydrogen, and an alkyl group having 1 to 4 carbon atoms, or $R^7$ and $R^8$ together form a —C(O)—O—(O)C— group. More preferably, $R^7$ and $R^8$ together form a —C(O)—O—(O)C— group. $R^7$ and $R^8$ together may also form a —C(O)—$NR^{10}$—C(O)— group, wherein $R^{10}$ represents hydrogen, an aliphatic or an aromatic group. When $R^{10}$ is an aromatic or aliphatic group it may be optionally substituted. Suitable substituents include hydroxyl, alkoxy, carbonyl, amino and hydrocarbonaceous groups. $R^{10}$ may suitably be selected from alkyl and aromatic groups. The alkyl group has typically from 1 to 15 carbon atoms, preferably from 1 to 6 carbon atoms. $R^{10}$ is suitably an aromatic group, which may be a heterocyclic aromatic moiety or a hydrocarbonaceous aromatic moiety. $R^{10}$ is preferably a hydrocarbonaceous aromatic moiety with 6 to 10 carbon atoms, more preferably a phenyl group.

The Diels-Alder reaction of the furan derivative of formula (I) with the olefin of formula (11) can be carried out at a broad variety of reaction conditions. Although elevated pressures may be applied, e.g., from 1 to 100 bar, more preferably, from 1 to 10 bar, it is most feasible to conduct the reaction at autogenous pressure. The reaction temperature may also vary from far below 0° C. to elevated temperatures. Suitably, the reaction temperature varies from 0° C. to 150° C., preferably from 20° C. to 100° C.

Known Diels-Alder catalysts may be used in the reaction. Suitable catalysts include Lewis acids, e.g., aluminium, boron, zinc, hafnium, lithium or iron compounds, such as $AlCl_3$, $Al(Et)Cl_2$, $Al(Et)_2Cl$, $BF_3$, $B(Ac)_3$, $ZnCl_2$, $ZnBr_2$, $Zn(Ac)_2$, $HfCl_4$, $FeCl_3$, $Fe(Ac)_3$, $FeCl_2$ and $Fe(Ac)_2$, $Zn(OTf)_2$ (zinc triflate), LiOTf, Li (bisoxalato)borate, but also halides of tin or titanium, such as $SnCl_4$ and $TiCl_4$. When a catalyst is used, the amount thereof may vary within wide ranges, such as from 0.01 to 50% mol, based on the furan compound of formula (I) or the olefin of formula (II), whichever is present in the lowest molar amount. Preferably, the amount of Diels-Alder catalyst is in the range of 0.1 to 20% mol, more preferably from 0.2 to 15% mol, based on the amount of the furan compound of formula (I) or the olefin of formula (II), whichever is present in the lowest molar amount. However, dependent on the electron donating behavior of the substituents on the furan compound and the electron withdrawing nature of the substituents on the olefin, the reactants may be so reactive that a catalyst is not needed to make the reaction occur. Evidently, in such a case the skilled person may decide not to use a catalyst in view of economic considerations.

Although it is possible to conduct the present reaction between the furan derivative and the olefin in the presence of a solvent, it is preferred to refrain from employing a solvent. Nevertheless, in certain cases the use thereof may be convenient. The use of a solvent is convenient if the furan derivative and/or the unsaturated bicyclic ether that is being produced is solid under the reaction conditions. The liquid phase thus obtained makes it easier to handle the reactant and/or the reaction products. Thereto, the solvent may be selected from a wide range of potential liquids. Suitably, the solvent is selected from the group consisting of water, alcohols, esters, ketones, amides, aldehydes, ethers, ionic liquids and sulphoxides.

Advantageously, the solvents contain from 1 to 20 carbon atoms. Examples of suitable alcohols include $C_1$-$C_4$ alcohols, in particular methanol, ethanol, n-propanol, isopropanol, butanol-1, butanol-2, 2-methylpropanol and tert-butanol. Suitable esters include the $C_1$-$C_{10}$ alkyl esters of $C_1$-$C_8$ carboxylic acids, such as methyl formate, methyl acetate, ethyl formate, ethyl acetate, methyl propionate, ethyl propionate, methyl butyrate, ethyl butyrate and ethylhexyl acetate. Suitable ketones contain 2 to 8 carbon atoms, such as acetone, butanone and methyl iso-butyl ketone. Suitable amides include acetamide and formamide, optionally substituted by one or two alkyl groups with 1 to 6 carbon atoms, such as N,N-dimethyl acetamide. Examples of suitable ethers include dialkyl ethers wherein each alkyl moiety is selected from a $C_1$-$C_6$ alkyl group, such as dimethyl ether, diethyl ether and methyl tert-butyl ether, and also cyclic ethers such as tetrahydrofuran or dioxane. Suitable aldehydes include $C_1$-$C_6$ aldehydes, such as formaldehyde, acetaldehyde, propanal and hexanal. Suitable ionic liquids comprise a pyridinium or imidazolinium moiety. Examples include pyridinium chloride, 1-ethyl-3-methylimidazolium dicyanamide and 1-butyl-3,5-dimethylpyridinium bromide. A suitable sulphoxide is dimethylsulphoxide.

The relative amounts of the furan derivative of formula (I) and the olefin of formula (II) may vary. Since stoichiometry shows that one mole of furan may react with one mole of olefin, the molar ratio of the amount furan derivative to the amount of olefin generally will be about 1:1, although the person skilled in the art may decide to provide one of the reactants in excess to promote the reaction and/or to facilitate the complete conversion of the other reactant. Therefore, the molar ratio between the amount of furan derivative to the amount of olefin suitably ranges from 0.1:1 to 10:1, preferably from 0.5:1 to 2:1, most preferably about 1:1.

For the Diels-Alder reaction, the reactants may be added in a batch-wise or a continuous fashion. In a batch-wise fashion both the furan derivative and olefin are charged to a vessel, e.g. an autoclave, and made to react with each other. Typically one of the reactants may be added in portions, over a period of time, to the other reactant, e.g. by using a syringe as described in US 2010/0127220. If desired, the reaction mixture is maintained at a desired temperature for a period of time, e.g. whilst stirring to increase the yield of product.

In a continuous fashion both a stream of furan derivative and a stream of olefin are fed to a reactor where they are contacted and from which reactor continuously a stream of product is withdrawn. The flow rate in a continuous reactor should be adapted such that the residence time is sufficient to allow a satisfactory conversion of the furan derivative and olefin. The Diels-Alder reaction is suitably carried out in a batch or continuous reactor wherein the residence time is from 0.1 to 72 hours, preferably from 0.5 to 48 hours.

When the process is conducted in a continuous mode, the reactor may be selected from various types of reactors, e.g. a continuous stirred tank reactor, a plug flow reactor or a trickle bed reactor when a solid catalyst is used.

The unsaturated bicyclic ether thus obtained is subsequently hydrogenated. Thereto the unsaturated bicyclic ether is suitably contacted with a reducing agent. Possible reducing agents include hydrides, such as LiH, NaH, $NaAlH_4$, $LiAlH_4$, $NaBH_4$ and $CaH_2$. However, the use of gaseous hydrogen is preferred. When hydrogen gas is used as hydrogenation agent the use of a hydrogenation catalyst is desired. Accordingly, the present invention preferably is conducted in a process wherein the unsaturated carbon-carbon bond in the unsaturated bicyclic ether is hydrogenated using gaseous hydrogen in the presence of a hydrogenation catalyst. Suitable hydrogenation catalysts comprise one or more metals or metal compounds selected from the metals in the Groups 8 to 10 of the Periodic Table of Elements, preferably on a carrier. Such suitable metals include Pt, Pd, Ru, Rh, Ir, Os, Ni, Co and mixtures thereof.

The carriers for these metals may be selected from a variety of conventional carriers. Preferably, the carrier has been selected from alumina, silica, titania, zirconia, silica-alumina, carbon, more preferably activated carbon, and mixtures thereof. The loading of the metal or metals on the carrier may also be varied within wide ranges. The content of metal on the hydrogenation catalyst may be in the range of 0.5 to 25% wt, more suitably from 1 to 10% wt, based on the weight of the hydrogenation catalyst.

Although the hydrogenation catalyst may be selected from any combination of the metals and carriers that are described herein, the most preferred hydrogenation catalyst is selected from palladium, platinum or ruthenium on activated carbon, in particular palladium on activated carbon.

It may be convenient to hydrogenate the unsaturated carbon-carbon bond in the unsaturated bicyclic ether in the presence of a solvent. The use of a solvent may render it easier to handle and to disperse the hydrogenation catalyst uniformly in the mixture of unsaturated bicyclic ether, gaseous hydrogen and solvent. The solvent may also facilitate the uptake of hydrogen, which promotes the hydrogenation reaction. When a solvent is used the solvent can suitably be selected from the group consisting of hydrocarbons, alcohols, esters, ketones, amides, aldehydes, ethers, ionic liquids and sulphoxides. It is advantageous to use a solvent that is not subjected to possible hydrogenation itself. Therefore, the use of saturated hydrocarbons or ethers is more suitable. Such suitable solvents, therefore, include $C_4$-$C_{10}$ aliphatic hydrocarbons or mixtures thereof and saturated ethers such as dialkyl ethers, wherein each alkyl moiety is selected from a $C_1$-$C_6$ alkyl group, or mixtures thereof, or cyclic ethers such as dioxane and tetrahydrofuran. Good results have been obtained by using a solvent that has been selected from the group consisting of saturated hydrocarbons and ethers, in particular cyclic ethers.

The hydrogenation conditions may vary within wide ranges. The skilled person will realize that the conditions may also be varied in accordance with the nature of the substituents. In order to selectively hydrogenate the unsaturated carbon-carbon bond in the unsaturated bicyclic ether, the hydrogenation temperature is kept at a moderate level. Low temperatures were found to reduce the retro Diels-Alder reactions. Suitably, the unsaturated bicyclic ether is hydrogenated at a temperature of 0 to 150° C., preferably from 10 to 100° C., more preferably from 20 to 80° C.

The hydrogen pressure may also be selected within a broad range. The unsaturated bicyclic ether is suitably hydrogenated at a hydrogen pressure of 1 to 125 bar, preferably at a hydrogen pressure of 10 to 100 bar. The reaction is completed when no hydrogen is taken up anymore. The duration of the hydrogenation reaction may typically be in the range of 0.5 to 24 hrs, suitably from 2 to 16 hrs.

Surprisingly the hydrogenation reaction can be substantially quantitative. Thus the saturated bicyclic ether is obtained in excellent yield and purity. If desired, the hydrogenated saturated bicyclic ether may be purified. This may be accomplished by washing the saturated bicyclic ether and/or by recrystallization from a suitable solvent. Such solvents can be selected from alcohols, hydrocarbons, esters, ethers and mixtures thereof.

The saturated bicyclic ether is then subjected to dehydration and aromatization. Since in the dehydration also hydrogen is liberated, the process according to the present invention does not require net hydrogen addition.

According to WO 2013/048248 the dehydration of the unsaturated bicyclic ether can be accomplished in the presence of a catalyst. The catalyst may be acidic or alkaline. A preference is expressed for an alkaline catalyst, such as an alcoholate, hydroxide, carboxylate or carbonate. Also in the process according to the present invention the saturated bicyclic ether is suitably dehydrated and aromatized in the presence of a catalyst. Different from the preference in WO 2013/048248, it has now surprisingly been found that the dehydration and aromatization of the saturated bicyclic ether is suitably performed in the presence of an acid catalyst. The acid catalyst can be a homogeneous or a heterogeneous catalyst. The use of a homogeneous catalyst boils down to a process wherein the reaction is carried out in a homogeneous liquid phase and the catalyst is comprised in that liquid phase. Suitable homogeneous catalysts that may be dissolved in the appropriate solvent to yield a homogeneous catalytic environment include organic and inorganic acids, such as alkane carboxylic acid, arene carboxylic acid, alkane sulphonic acid, such as methane sulphonic acid, arene sulphonic acid, such as p-toluene sulphonic acid, sulphuric acid, phosphoric acid, hydrochloric acid, hydrobromic acid and nitric acid. When an arene carboxylic acid is the eventually desired product, such as phthalic acid, methylphthalic acid, isophthalic acid or hemimellitic acid, a preferred arene carboxylic acid is selected from phthalic acid, methylphthalic acid, isophthalic acid and hemimellitic acid, since these acids provides catalytic activity and do not add an extraneous chemical to the reaction mixture.

Preferably, the dehydration and aromatization is carried out in the presence of a heterogeneous catalyst. When a heterogeneous catalyst is used, the reaction is conducted in a liquid reactant phase and a solid catalyst phase. Hence, the catalyst is preferably a solid catalyst. Examples of solid acidic catalysts include amorphous silica-alumina, zeolites, preferably zeolites in their H-form, phosphoric acid on a carrier, sulfonated activated carbon and acidic ion exchange resins, wherein zeolites, ion exchangers, sulfonated activated carbon and combinations thereof are preferred. Zeolites are particularly preferred. Zeolites are the preferred catalysts since they can withstand relatively high reaction temperatures and their acidity can be adjusted by selecting the desired level of ion exchange of metal ions by protons and/or by varying the silica-alumina ratio in the zeolite. The zeolite can be selected from a variety of zeolitic structures. In principle all zeolitic structures as defined in the Database of Zeolite Structures and approved by the Structure Committee of the International Zeolite Association can be used. Good results have been obtained with the zeolites selected from the group consisting of zeolite Y, zeolite X, zeolite beta, mordenite and mixtures thereof. Zeolites are crystalline aluminosilicates that contain certain alkali and alkaline earth cations, such as sodium or magnesium ions. By varying the silica/alumina ratio and by varying the removal of the alkali and alkaline earth metal cations and replacing them by protons, the acidity of the zeolite can be adjusted. Typically, the zeolite has a silica/alumina molar ratio in the range of 1 to 200. Suitably the zeolite has been subjected to ion exchange to remove alkaline and alkaline earth cations and have these cations replaced by protons. An alternative preferred solid acidic catalyst is sulfonated activated carbon. This catalyst comprises sulfonic acid groups attached to activated carbon. The preparation thereof has e.g. been described in Liu et al, Molecules, 2010, 15, 7188-7196.

The skilled person will realize that the amount of acidic catalyst can be varied within broad ranges. It has been found that it is advantageous to use the acidic catalyst in an amount in the range of 10% wt to 50% wt, based on the amount of substrate, i.e. the saturated bicyclic ether. When smaller amounts of catalyst are used the reaction may take longer.

It is advantageous to dehydrate and aromatize the saturated bicyclic ether neat. This promotes the contact of the saturated bicyclic ether with the catalyst. In other embodiments it is desirable to conduct the dehydration and aromatization in the presence of a solvent. The dispersion of the solid catalyst is then facilitated. If a solvent is used, the nature of the solvent is not critical, and the solvent can suitably be selected from the group consisting of aliphatic and aromatic hydrocarbons, alcohols, esters, ketones, amides, aldehydes, ethers, ionic liquids and sulphoxides, preferably hydrocarbons, more preferably, aromatic hydrocarbons. The use of aromatic hydrocarbon solvents is preferred since the solubility of the eventual benzene compound tends to be high in the aromatic hydrocarbon solvent. Preferably, the aromatic hydrocarbon solvent is toluene, xylene or a mixture thereof.

In the dehydration and aromatization reaction not only water is split off from the saturated bicyclic ether, but also one molecule of hydrogen per molecule of saturated bicyclic ether is removed during the dehydration and aromatization. It has therefore been considered to employ a dehydrogenation catalyst, in addition to an acidic catalyst that promotes the dehydration. Dehydrogenation catalysts include metal oxides as well as metals, usually on a carrier. Suitable catalysts include chromia and iron oxide as examples of a metal oxide catalyst, and noble metals, such as Pt, Pd, Ru and Rh, on activated carbon as supported metal catalyst.

Although the use of such catalysts allow for more modest reaction conditions, such as a relatively low temperature, it has been found that the catalyst also promotes the formation of saturated by-products. Without wishing to be bound by any theory, it is believed that hydrogen that is split off from the saturated bicyclic ether to form a benzene compound, is subsequently used to hydrogenate another molecule to form a cyclohexene compound. This reaction is believed to be promoted by a dehydrogenation catalyst.

When the dehydration and aromatization is carried out in the absence of a solvent, the dehydration and aromatization step is preferably conducted in the presence of a solid acidic catalyst and in the absence of a dehydrogenation catalyst. When a solvent is present in the dehydration and aromatization step, it is suitable to include also a dehydrogenation catalyst.

The dehydration and aromatization occurs at a reaction temperature that is preferably in the range of 100 to 350° C., preferably from 125 to 275° C. When also a dehydrogenation catalyst and a solvent are present in the reaction mixture, the temperature is suitably somewhat lower, such as from 75 to 250° C., preferably from 100 to 200° C. The atmosphere is typically inert; the reaction is suitably carried out under nitrogen, helium, neon or argon. The pressure in the dehydration and aromatization step is preferably ranging from 0.5 to 50 bar. The saturated bicyclic ether is suitably dehydrated and aromatized in a batch or continuous reactor wherein the residence time is from 0.1 to 48 hours.

The present process is excellently suited for the preparation of aromatic acids, such as methylphthalic acid or anhydride and hemimellitic acid. It is also possible to prepare other benzene compounds, such as benzene, toluene, xylene, benzoic acid, toluic acid, and similar compounds, in this way. Via this route the provision of these acids or these other benzene compounds from a sustainable source has become available. The furan compound of formula (I) can be prepared from the conversion of carbohydrates, as explained in WO 2013/048248 and WO 2007/104514. Therefore, the present invention also provides the preparation of a substituted benzene compound wherein the benzene compound produced by the dehydration and aromatization of the saturated bicyclic ether is oxidized. In this way the substituents on the benzene compound that contain a carbon atom are converted into carboxylic acid groups.

The oxidation may be conducted in a known manner. Thereto, the oxidation is suitably accomplished by an oxygen-containing gas in the presence of a catalyst comprising cobalt and manganese or by alkali metal permanganate, such as potassium permanganate, or nitric acid. Aromatic carboxylic acids may suitably be prepared over a catalyst that contains bromine in addition to cobalt and manganese. Preparation of such a catalyst has, for instance, been described U.S. Pat. No. 4,138,354. The oxygen-containing gas may be air, oxygen-enriched air or substantially pure oxygen. When the benzene compound contains an oxygen atom in its substituents, other, more conventional and/or less expensive catalysts are also possible since such benzene compounds are more reactive and easier to oxidize than benzene compounds that do not have an oxygen atom in their substituents. Therefore, oxidation using potassium permanganate, nitric acid, or using oxygen over noble metal-containing catalyst (e.g., Rh, Pd) is also possible.

The temperature and pressure of the oxidation can be selected within wide ranges. The pressure of the reaction mixture is preferably between 1 and 100 bar, with a preference for pressures between 10 and 80 bar. In case the oxidant is an oxygen-containing gas, such as air, the gas can be continuously fed to and removed from the reactor, or all of the gas can be supplied at the start of the reaction. In the latter case, the pressure of the system will depend on the headspace volume and the amount of gas required for converting the starting material. It is clear that in the latter case, the pressure of the system may be significantly higher than when an oxygen-containing gas is continuously fed and removed.

The temperature of the reaction mixture at the oxidation is suitably between 60 and 300° C., preferably between 100 and 260° C., more preferably between 150 and 250° C., most preferably between 160 and 220° C.

In the preferred oxidation catalysts that comprise Co and Mn, molar ratios of cobalt to manganese (Co/Mn) are typically 1/1000-100/1, preferably 1/100-10/1 and more preferably 1/10-4/1.

Likewise, in these preferred oxidation catalysts, comprising also bromine, molar ratios of bromine to metals (i.e. Br/(Co+Mn)) are typically from 0.001 to 5.00, preferably 0.01 to 2.00 and more preferably 0.1 to 0.9.

Catalyst concentration (calculated on the metal, e.g., Co+Mn) is preferably between 0.1 and 10 mol % relative to the starting material, with a preference for loads between 2 and 6 mol %. Good results will be obtained in general with catalyst loads of around 4 mol % relative to the starting benzene compound.

Reaction times suitably range from 0.1 to 48 hours, preferably from 0.5 to 24 hrs. The skilled person will realize that the number of carboxylic groups on the benzene ring may be varied. He may vary this number by selecting the appropriate starting materials. Alternatively, he may want to decarboxylate the products, using a method similar to the one described in U.S. Pat. No. 2,729,674 for the mono-decarboxylation of trimellitic acid. Such decarboxylation involves the application of a relatively high temperature, such as from 200 to 400° C. Since decarboxylation may occur at temperatures of about 200° C., some decarboxylation may already occur when the aromatization of the saturated bicyclic ether is carried out at temperatures of at least 200° C. and when the saturated bicyclic ether contains carboxylic groups as substituents. In the process of the present invention decarboxylation may be used to arrive at the desired benzene compound. By applying longer reaction times and/or higher reaction temperatures, the rate of decarboxylation can be influenced. It was also found that the decarboxylation readily occurs at temperatures from 200° C. when the aromatization is carried out in the absence of a solvent. When a solvent is present in the aromatization step, significantly higher temperatures are required to accomplish significant decarboxylation. Another known decarboxylation process uses a diazabicyclo alkene at elevated temperatures as shown in U.S. Pat. No. 4,262,157.

The invention enables the provision of certain novel intermediate compounds. Accordingly the present invention provides the hydrogenated Diels-Alder adduct of the formula (III)

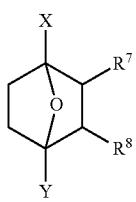

(III)

wherein X and Y are different and independently selected from the group consisting of hydrogen, alkyl, aralkyl, —CHO, —CH$_2$OR$^3$, —CH(OR$^4$)(OR$^5$), —COOR$^6$, wherein R$^3$, R$^4$ and R$^5$ are the same or different and are independently selected from the group consisting of hydrogen, alkyl, aryl, alkaryl, aralkyl, alkylcarbonyl and arylcarbonyl, or wherein R$^4$ and R$^5$ together form an alkylene group, and wherein R$^6$ is selected from the group consisting of hydrogen, alkyl and aryl; and wherein R$^7$ and R$^8$ are the same or different and are independently selected from the group consisting of sulfonate, —CN, —CHO, and —COOR$^9$, wherein R$^9$ is selected from the group consisting of hydrogen, and an alkyl group, or R$^7$ and R$^8$ together form a —C(O)—O—(O)C— group or a —C(O)—NR$^{10}$—C(O)— group, wherein R$^{10}$ represents hydrogen, an aliphatic or an aromatic group. The hydrogenated Diels-Alder adduct is an oxa-[2,2,1]-bicyclo-heptane compound.

More in particular the invention provides a hydrogenated Diels-Alder adduct of formula (IV)

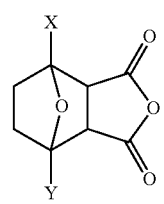

(IV)

wherein X and Y are different and independently selected from the group consisting of hydrogen, —CHO, —CH$_2$OR$^3$, —COOR$^4$, wherein R$^3$ is selected from the group consisting of hydrogen, alkyl, aryl, alkaryl, aralkyl, alkylcarbonyl and arylcarbonyl, and wherein R$^4$ is selected from the group consisting of hydrogen, alkyl and aryl It has further been found that the dehydration and aromatization reaction of the saturated bicyclic ether yields a lactone. It is believed that this lactone is an intermediate product in the formation of the eventual benzene compound. This benzene compound can therefore be prepared by subjecting such a lactone to the same reaction conditions as the desired for the formation of the benzene compound from the saturated bicyclic ether. The present invention therefore also provides a lactone compound of formula (V)

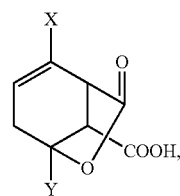

(V)

wherein Y is hydrogen and X is selected from the group consisting of alkyl, aralkyl, —CHO, —CH$_2$OR$^3$, —CH(OR$^4$)(OR$^5$), —COOR$^6$, wherein R$^3$, R$^4$ and R$^5$ are the same or different and are independently selected from the group consisting of hydrogen, alkyl, aryl, alkaryl, aralkyl, alkylcarbonyl and arylcarbonyl, or wherein R$^4$ and R$^5$ together form an alkylene group, and wherein R$^6$ is selected from the group consisting of hydrogen, alkyl and aryl.

More preferably, Y is hydrogen and X is selected from the group consisting of alkyl, aryl, alkaryl, aralkyl, —CHO, or —CH$_2$OR$^3$, wherein R$^3$ is selected from the group consisting of hydrogen, alkyl and aryl. The alkyl, aryl, aralkyl or alkaryl groups suitably have at most 10 carbon atoms. The alkyl groups may preferably have from 1 to 4 carbon atoms.

The invention will be illustrated by means of the following examples.

EXAMPLE 1

Diels-Alder Reaction of (Substituted) Furan and Maleic Anhydride

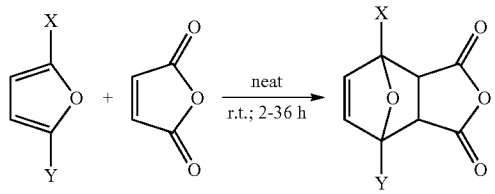

A round-bottom flask equipped with water-cooled condenser and mechanical over-head stirrer was charged with a furan compound as indicated in Table 1 (1.2 mmol) and maleic anhydride (1.0 mmol). The suspension was stirred at 15-20° C. using a water bath. During the course of the reaction, the mixture turned to a clear homogeneous liquid after a reaction time as indicated in Table 1. Pale-yellow colored crystalline material crystallized from the liquid. The yield was as indicated in Table 1, relative to the molar amount of maleic anhydride. $^1$H NMR spectroscopy further revealed the purities of the adducts, as shown in Table 1. Percentages are molar percentages, based on the number of moles of maleic anhydride.

The results and conditions are shown in Table 1.

TABLE 1

| Exp. No. | X | Y | Reaction time, hr | Yield, % | Purity, % |
|---|---|---|---|---|---|
| 1 | —H | —H | 3 | 98 | 94 |
| 2 | —CH$_3$ | —H | 4 | >95 | 93 |
| 3 | —CH$_3$ | —CH$_3$ | 3 | 96 | 94 |
| 4 | —CH$_2$—O—CH$_3$ | —H | 18 | >85 | 80 |
| 5 | —CH$_2$—O—C$_2$H$_5$ | —H | 26 | >85 | 80 |

EXAMPLE 2

Hydrogenation of Diels-Alder Adduct from Furan Compounds and Maleic Anhydride

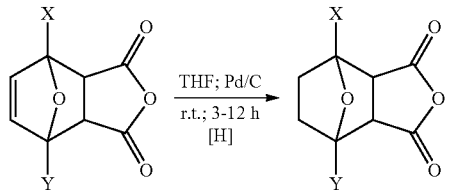

A pressure reactor was charged with 100 parts by weight (pbw) of crude adduct obtained in Example 1 (see Table 2), 2 pbw of catalyst Pd/C (containing 10% wt Pd, based on the catalyst), and THF in a quantity of 5 mL per gram adduct. The reactor was purged 3 times with nitrogen of 4-5 bar, and then pressurized with hydrogen to 80 bar. The reaction mixture was stirred at room temperature at 300 rpm. During the progress of the reaction the hydrogen pressure dropped, but the reactor was subsequently re-pressurized to 80 bar. When the consumption of hydrogen gas stopped, the reaction was completed. The reaction time is indicated in Table 2. Excess hydrogen pressure was cautiously vented off and the reactor was flushed 3 times with nitrogen of 4-5 bar. The mixture was filtered yielding a pale yellow clear solution, which was evaporated to dryness under reduced pressure using a rotary evaporator. The crude product was further purified by recrystallization from methanol or ethyl acetate which resulted in hydrogenated Diels-Alder adduct as colorless solid in a yield and with a purity, as determined by NMR and GC analysis and indicated in Table 2. Percentages are molar percentages, based on starting material (yield) or on product.

TABLE 2

| Exp. No. | X | Y | Reaction time t, hrs | Yield, % | Purity, % |
|---|---|---|---|---|---|
| 6 | —H | —H | 3-5 | ~100 | 96 |
| 7 | —CH$_3$ | —H | 3-5 | ~100 | 95 |
| 8 | —CH$_3$ | —CH$_3$ | 3-5 | ~100 | 98 |
| 9 | —CH$_2$—O—CH$_3$ | —H | 5 | 89 | 90 |
| 10 | —CH$_2$—O—C$_2$H$_5$ | —H | 5 | 85 | 89 |

EXAMPLE 3

Diels-Alder Reaction of Substituted Furan and Methyl Acrylate

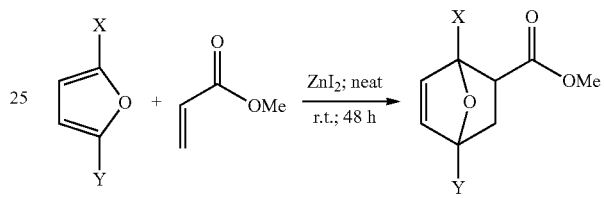

A round-bottom flask equipped with water-cooled condenser and mechanical over-head stirrer was charged with a furan compound as indicated in Table 3 (1.2 mmol), methyl acrylate (1.0 mmol) and zinc iodide (0.3 mmol). The suspension was stirred at 40° C. for 48 h. After the completion of reaction, the mixture was diluted with ethyl acetate and washed with 0.1M aqueous solution of Na$_2$S$_2$O$_3$, dried and concentrated to afford pale-yellow colored liquid. The yield was as indicated in Table 3.

TABLE 3

| Exp. No. | X | Y | Reaction Time (h) | Yield (%) |
|---|---|---|---|---|
| 11 | CH$_3$ | H | 48 | 43 |
| 12 | CH$_3$ | CH$_3$ | 48 | 45 |

EXAMPLE 4

Hydrogenation of Diels-Alder Adduct from Furan Compounds and Methyl Acrylate

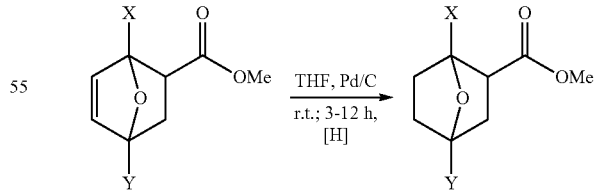

A pressure reactor was charged with 100 parts by weight (pbw) of crude adduct obtained in Example 3 (see Table 4), 2 pbw of catalyst Pd/C (containing 10% wt Pd, based on the catalyst), and THF in a quantity of 5 mL per gram adduct. The reactor was purged 3 times with nitrogen of 4-5 bar, and then pressurized with hydrogen to 80 bar. The reaction mixture was stirred at room temperature at 300 rpm. During the progress of the reaction the hydrogen pressure dropped, but the reactor was subsequently re-pressurized to 80 bar. When the consumption of hydrogen gas stopped, the reaction was completed. The reaction time is indicated in Table 4. Excess hydrogen pressure was cautiously vented off and the reactor was flushed 3 times with nitrogen of 4-5 bar. The mixture was filtered yielding a pale yellow clear solution, which was evaporated to dryness under reduced pressure using a rotary evaporator. The crude product was further purified by a short filtration through silica gel affording hydrogenated Diels-Alder adduct, an oxa-bicyloheptane compound with a methylcarboxylate substituent on the 2- or 3-position, as pale-yellow coloured liquid.

TABLE 4

| Exp. No. | X | Y | Reaction Time (h) | Yield (%) |
|---|---|---|---|---|
| 13 | $CH_3$ | H | 12 | 90 |
| 14 | $CH_3$ | $CH_3$ | 12 | 92 |

EXAMPLE 5

Aromatization of Hydrogenated Diels-Alder Adduct Over Acid and Dehydrogenation Catalysts

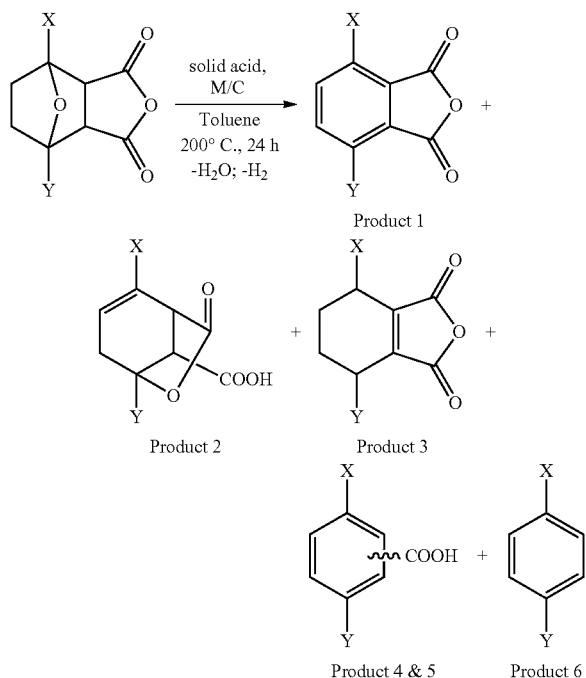

Product 1

Product 2

Product 3

Product 4 & 5

Product 6

A stainless steel pressure reactor was charged with the products obtained in experiments 7 and 8 of Example 2 (see Table 2) (1.0 mmol), an acid zeolite Y catalyst in an amount of 50 pbw per 100 pbw of the product of experiments 7 and 8 of Example 2, respectively, 3 pbw of Pd/C (10 wt % of Pd based on the weight of the catalyst) and toluene (20 mL/g product). Next, the reactor was purged 3 times with nitrogen of 10 bar, and the reaction mixture was stirred (750 rpm) at 150-200° C. for 24 h. During the course of reaction, the pressure rose to a maximum of 6-8 bar. After completion of the reaction, the reactor was cooled down to room temperature and the excess pressure was carefully vented off. The crude reaction mixture was filtered using a filter aid and washed 5 times with 10 mL toluene, giving a pale yellow clear solution, which was then evaporated to dryness under reduced pressure using a rotary evaporator to give yellow colored crystalline material. The analysis of crude product using $^1H$ NMR spectroscopy confirmed the formation of desired aromatic compound, viz. optionally substituted phthalic anhydride together with up to four different by-products (based on the catalyst used). The products distribution was calculated by NMR analyses, using 1,4-dinitrobenzene as internal standard.

The yields of the respective products are shown in Table 5. Percentages are molar percentages, based on starting material.

TABLE 5

| Exp. No. | X | Y | Acid catalyst | Dehydrog. Catalyst | Yield of Product, % | | | | |
|---|---|---|---|---|---|---|---|---|---|
| | | | | | 1 | 2 | 3 | 4&5 | 6 |
| 15 | —$CH_3$ | —$CH_3$ | H—Y | Pd/C | 67 | — | — | 12* | — |
| 16 | $CH_3$ | —H | H—Y | Pd/C | 59 | 0 | 0 | 21 | —+ |

*in this case, it is para-xylene.
+ any toluene formed was not detectable as the reaction was performed in toluene as solvent

EXAMPLE 6

Aromatization of Hydrogenated Diels-Alder Adduct Over Acid Catalyst

In experiment Nos. 17 and 18 a round-bottom flask was charged with each of the products obtained in Example 4 (1.0 mmol) and solid acid catalyst (100 pbw per 100 pbw of product). The acid catalyst was selected from an acid zeolite Y with a silica-alumina ratio of 5.2 ("H—Y"). Next, the flask was purged 3 times with nitrogen and inserted into a glass oven at 200° C. The reaction flask was rotated at 25 rpm for about 2.0 hr under nitrogen atmosphere. After completion of the reaction, the glass oven was cooled down to room temperature. The crude reaction mixture was dissolved in chloroform ($CDCl_3$) and filtered and washed 3 times with 10 mL $CDCl_3$, giving a pale yellow clear solution, which was then evaporated to dryness under reduced pressure using a rotary evaporator. A yellow colored crystalline material was thus obtained. The analysis of crude product using $^1H$ NMR spectroscopy confirmed the formation of desired benzene compound, i.e. the benzene compound with a carboxylate moiety on the 2- or 3-position, and the calculated product yield about was 20-30% molar.

EXAMPLE 7

Solvent-Free Aromatization of Hydrogenated Diels Alder Adduct Over Acid Catalyst

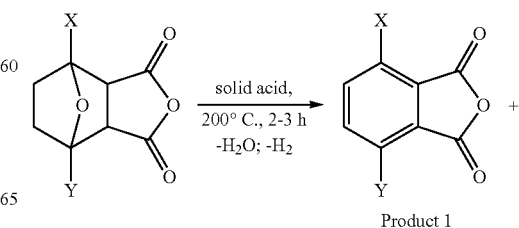

Product 1

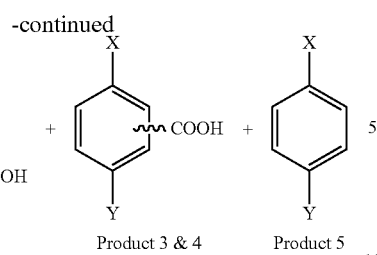

Product 2  Product 3 & 4  Product 5

A round-bottom flask was charged with a product obtained in Example 2 (1.0 mmol) and solid acid catalyst (100 pbw per 100 pbw of product). The acid catalyst was selected from an acid zeolite Y with a silica-alumina ratio of 5.2 ("H—Y"), such zeolite Y catalyst that contained 1% wt Pd ("Pd/H—Y"), such zeolite Y catalyst that contained 0.25% wt Pt and 0.25% wt Pd ("Pt/Pd/H—Y"). Next, the flask was purged 3 times with nitrogen and inserted into a glass oven at 200° C. The reaction flask was rotated at 25 rpm for about 2 to 3 hr under nitrogen atmosphere. After completion of the reaction, the glass oven was cooled down to room temperature. The crude reaction mixture was dissolved in chloroform ($CDCl_3$) and filtered and washed 3 times with 10 mL $CDCl_3$, giving a pale yellow clear solution, which was then evaporated to dryness under reduced pressure using a rotary evaporator. A yellow colored crystalline material was thus obtained. The analysis of crude product using $^1H$ NMR spectroscopy confirmed the formation of desired aromatic compound, viz. optionally substituted phthalic anhydride together with up to three different by-products (dependent on the catalyst used). The product distribution in the crude mixture was calculated by NMR analyses using 1,4-dinitrobenzene as internal standard.

The compounds, the catalyst used, and the yields of the respective products are shown in Table 7. Percentages are molar percentages, based on starting material.

TABLE 7

| Exp. | | | Acid | Yield of Product, % | | | |
|---|---|---|---|---|---|---|---|
| No. | X | Y | catalyst | 1 | 2 | 3&4 | 5 |
| 19 | —H | —H | H—Y | 41 | — | 26 | 23 |
| 20 | —$CH_3$ | —H | H—Y | 76 | — | 13 | — |
| 21 | —$CH_3$ | —$CH_3$ | H—Y | 72 | — | 11 | 17 |
| 22 | —$CH_3$ | —H | Pd/H—Y | 80 | — | 7 | —* |
| 23 | —$CH_3$ | —H | Pt/Pd/H—Y | 62 | — | 17 | —** |

*Experiment 22 also yielded 5% of 3-methyl-1,2-dicarboxylic anhydride-cyclohexene-1.
**Experiment 23 also yielded 10% of 3-methyl-1,2-dicarboxylic anhydride-cyclohexene-1.

EXAMPLE 8

Effect of Time and Temperature on the Aromatization of Saturated Bicyclic Ether Over Acid Catalyst

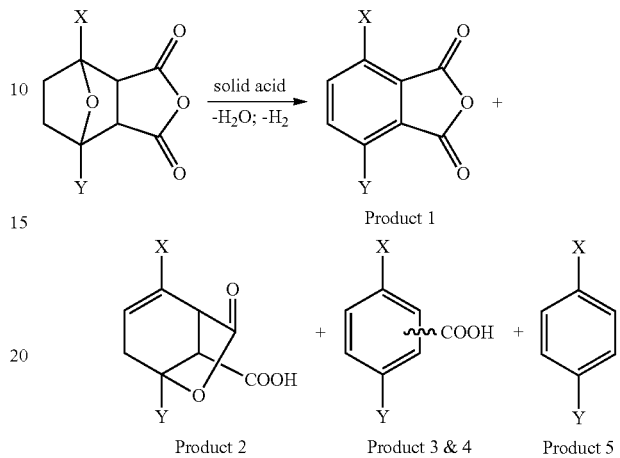

A round-bottom flask was charged with a product obtained in Example 2 (1.0 mmol) and solid acid catalyst (50 pbw or 100 pbw per 100 pbw of product). The acid catalysts used were the same as those used in Example 7. Next, the flask was purged 3 times with nitrogen and inserted into a glass oven at a fixed temperature. The reaction flask was rotated at 25 rpm for a fixed amount of time under nitrogen atmosphere. Subsequently, the glass oven was cooled down to room temperature. The crude reaction mixture was dissolved in chloroform ($CDCl_3$) and filtered and washed 3 times with 10 mL $CDCl_3$, giving a pale yellow clear solution, which was then evaporated to dryness under reduced pressure using a rotary evaporator. A yellow colored crystalline material was thus obtained. The analysis of crude product using $^1H$ NMR spectroscopy confirmed the formation of desired aromatic compound, viz. optionally substituted phthalic anhydride together with up to three different by-products (dependent on the catalyst used). The product distribution in the crude mixture was calculated by NMR analyses using 1,4-dinitrobenzene as internal standard.

The compounds, the catalyst used, and the yields of the respective products are shown in Table 8. Percentages are molar percentages, based on starting material.

TABLE 8

| Exp. | | | Temp. | Time | | Conv. | Yield of Product, % | | | |
|---|---|---|---|---|---|---|---|---|---|---|
| No. | X | Y | (° C.) | (hrs) | Acid catalyst | (%) | 1 | 2 | 3&4 | 5 |
| 24 | —$CH_3$ | —H | 150 | 2 | H—Y (50%) | 89 | 12 | 77 | 0 | 0 |
| 25 | —$CH_3$ | —H | 150 | 15 | H—Y (50%) | 100 | 34 | 66 | 0 | 0 |
| 26 | —$CH_3$ | —H | 160 | 2 | H—Y (50%) | 100 | 24 | 76 | 0 | 0 |
| 27 | —$CH_3$ | —H | 175 | 2 | H—Y (50%) | 100 | 37 | 63 | 0 | 0 |
| 28 | —$CH_3$ | —H | 160 | 2 | H—Y (100%) | 100 | 43 | 54 | 0 | 0 |
| 29 | —$CH_3$ | —H | 175 | 2 | H—Y (100%) | 100 | 81 | 9 | 6 | 0 |
| 30 | —$CH_3$ | —H | 200 | 2 | H—Y (100%) | 100 | 76 | 0 | 6 | 13 |
| 31 | —$CH_3$ | —H | 225 | 2 | H—Y (100%) | 100 | 45 | 0 | 0 | 55 |
| 32 | —$CH_3$ | —H | 250 | 5 | H—Y (100%) | 100 | 0 | 0 | 0 | 100 |
| 33 | —H | —H | 160 | 15 | H—Y (100%) | 43 | 15 | 28 | 0 | 0 |
| 34 | —H | —H | 200 | 2 | H—Y (100%) | 100 | 41 | 0 | 26 | 23 |
| 35 | —$CH_3$ | —$CH_3$ | 200 | 2 | H—Y (100%) | 100 | 72 | 0 | 11 | 17 |

The invention claimed is:
1. A hydrogenated Diels-Alder adduct of the formula (IV)

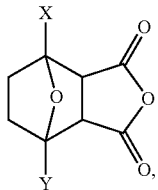

(IV)

wherein X and Y are different and independently selected from the group consisting of —CHO, —CH$_2$OR$^3$ and —COOR$^4$, wherein R$^3$ is selected from the group consisting of hydrogen, alkyl, aryl, alkaryl, aralkyl, alkylcarbonyl and arylcarbonyl, and wherein R$^4$ is selected from the group consisting of hydrogen, alkyl and aryl.

2. A lactone compound of formula (V)

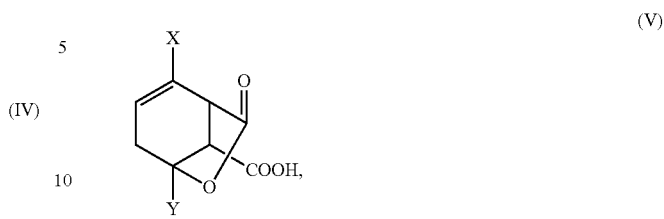

(V)

wherein Y is hydrogen and X is selected from the group consisting of alkyl, aralkyl, —CHO, —CH$_2$OR$^3$, —CH(OR$^4$)(OR$^5$), —COOR$^6$, wherein R$^3$, R$^4$ and R$^5$ are the same or different and are independently selected from the group consisting of hydrogen, alkyl, aryl, alkaryl, aralkyl, alkylcarbonyl and arylcarbonyl, or wherein R$^4$ and R$^5$ together form an alkylene group, and wherein R$^6$ is selected from the group consisting of hydrogen, alkyl and aryl.

3. The lactone compound according to claim 2, wherein Y is hydrogen and X is selected from the group consisting of alkyl, aralkyl, —CHO, or —CH$_2$OR$^3$, wherein R$^3$ is selected from the group consisting of hydrogen, alkyl and aryl.

* * * * *